United States Patent [19]

Giannini et al.

[11] Patent Number: 5,088,493
[45] Date of Patent: Feb. 18, 1992

[54] MULTIPLE WAVELENGTH LIGHT PHOTOMETER FOR NON-INVASIVE MONITORING

[75] Inventors: Ivo Giannini; Marco Ferrari; Amilcare C. de Resmini, all of Rome, Italy; Paolo Fasella, Bruxelles, France

[73] Assignee: Sclavo, S.p.A., Siena, Italy

[21] Appl. No.: 161,206

[22] Filed: Feb. 16, 1988

Related U.S. Application Data

[63] Continuation-in-part of Ser. No. 756,394, Jul. 17, 1985, abandoned.

[30] Foreign Application Priority Data

Aug. 7, 1984 [IT] Italy ............... 22247 A/84

[51] Int. Cl.⁵ .............................................. A61B 5/14
[52] U.S. Cl. ...................................... 128/633; 128/664
[58] Field of Search ............... 128/633, 634, 664–666

[56] References Cited

U.S. PATENT DOCUMENTS

| | | | |
|---|---|---|---|
| 3,638,640 | 2/1972 | Shaw | 128/633 |
| 4,086,915 | 5/1978 | Kofskey | 128/633 |
| 4,222,389 | 9/1980 | Rubens | 128/633 |
| 4,223,680 | 9/1980 | Jobsis et al. | 128/633 |
| 4,281,645 | 8/1981 | Jobsis | 128/633 |
| 4,295,470 | 10/1981 | Shaw et al. | 128/634 |
| 4,321,930 | 3/1982 | Jobsis | 128/633 |
| 4,380,240 | 4/1983 | Jobsis et al. | 128/633 |
| 4,427,889 | 1/1984 | Muller | 128/633 |
| 4,449,535 | 5/1984 | Renault | 128/634 |
| 4,510,938 | 4/1985 | Jobsis et al. | 128/633 |
| 4,513,751 | 4/1985 | Abe et al. | 128/666 |

OTHER PUBLICATIONS

Takatani et al., 30th ACEMB, Los Angeles, 5–9 Nov. 1977, p. 171.

Primary Examiner—Kyle L. Howell
Assistant Examiner—John Hanley
Attorney, Agent, or Firm—Hedman, Gibson & Costigan

[57] ABSTRACT

A multiple wavelength light spectrophometer for non-invasive monitoring of a body organ in vivo comprising: a single pulsed light source, optical fibers for transmitting to and receiving the infrared radiation from the organ, a radiation detector capable of branching received radiation into several different wavelengths, an amplifier, and a data acquisition system including a microprocessor capable of compensating for light diffusion effects by employing a specific algorithm.

6 Claims, 8 Drawing Sheets

MULTIPLE WAVELENGTH LIGHT PHOTOMETER FOR NON-INVASIVE MONITORING This application is a continuation-in-part of application Ser. No. 06/756,394, filed July 17, 1985, now abandoned.

BACKGROUND OF THE INVENTION

Significant developments in medical diagnostics have been brought about in recent years by the introduction of non-invasive methodics. Among these, near-infrared (I.R.) spectroscopy and instruments have been utilized to characterize biological tissues in vivo.

I. R. spectrophotometry rests upon the relative transparency of biological materials to photons in the near I. R. (700–900 nm). In situ photon transmission through organs is sufficient to permit monitoring of absorptive changes in the tissues. In this spectral region, only some chromophores of great functional significance absorb light: the heme of hemoglobin whereby changes in local hematic volume and equilibrium between oxyhemoglobin ($HbO_2$) and hemoglobin (Hb) can be assessed, and the visible copper of cytochromeoxidase (cyt $a,a_3$), i.e. the terminal enzyme in the mitochondrial respiratory chain which catalyzes 95% of the cell oxygen ($O_2$) input.

Since the mitrochondial respiratory chain is the main gateway to utilizing the free energy obtained in the various metabolisms, in vivo evaluation of the redox state of cyt $a,a_3$ may be of great assistance in assessing the functional state of cells in various physiopathological situations (E. Dora, J. Neurochem. 42, 101-108, 1984; M. Erecinska, D. Wilson, J. Memb. Biology 70, 1-14, 1982; E. F. Jobsis, Adv. Neurol. 26,299, 1979).

Fairly accurate methods are known of measuring the level of oxygenation in the hemoglobin circulating through the vascular system of surface tissues (Takatani et al., Ann. Biomed. Eng. 8,1 1980). In general, however, such prior methods fail to provide quantitative results with internal organs owing to the difficulty encountered in evaluating the effects of light diffusion.

Jobsis, of Duke University, recently proposed to use this type of spectroscopy to characterize cell metabolism in vivo (U.S. Pat. No. 4,281,645), and in particular, to assess the oxygenation level of cerebral tissues by measuring the I.R. absorption of cytomchrome-c-oxidase (F. F. Jobsis, Science, 198,1264, 1977).

The spectrophotometer proposed by Jobsis comprises: (A) some light sources which emit sequentially radiation within the range of 700 to 1,300 nm; (B) a fiber optic which transmits the light to an organ to be monitored; (C) an optical fiber which picks up the emerging radiation from the monitored organ; and (D) a system for converting the radiation to a readily analyzed signal.

However, the spectrophotometer proposed by Jobsis provides unacceptable quantitative results because it takes into no account the effects of light diffusion, which are quite significant and may vary over time; further, and more specifically, light diffusion makes the optical path non-rectilinear and Beer-Lambert law does not apply.

Thus, the instrument is unable to correct the observed data due to scattering effects.

SUMMARY OF THE INVENTION

Now, we have developed a spectrophotometer, forming the subject matter of this patent application, which can provide a quantitative and simultaneous assessment of the absorption due to cytochrome-c-oxidase and the two forms (oxygenated and non-oxygenated) of hemoglobin which are present in tissues in vivo, while taking into account the effects of light diffusion and of any variations thereof over time.

DESCRIPTION OF DRAWINGS

A better understanding of the invention may be had by reference to the detailed description which follows, taken in conjunction with the accompanying drawings, in which.

The most important applications of this type of instrumentation may regard the monitoring of the circulatory and metabolic conditions of the encephala of immature babies, patients who have undergone neurosurgery interventions, interventions of vascular surgery to the carotids, and in general patients under total anesthesia or being subjected to intensive therapy; further applaications may involve monitoring of the peripheral vascular system and cases of chronic or acute respiratory insufficiency.

Figure 1:
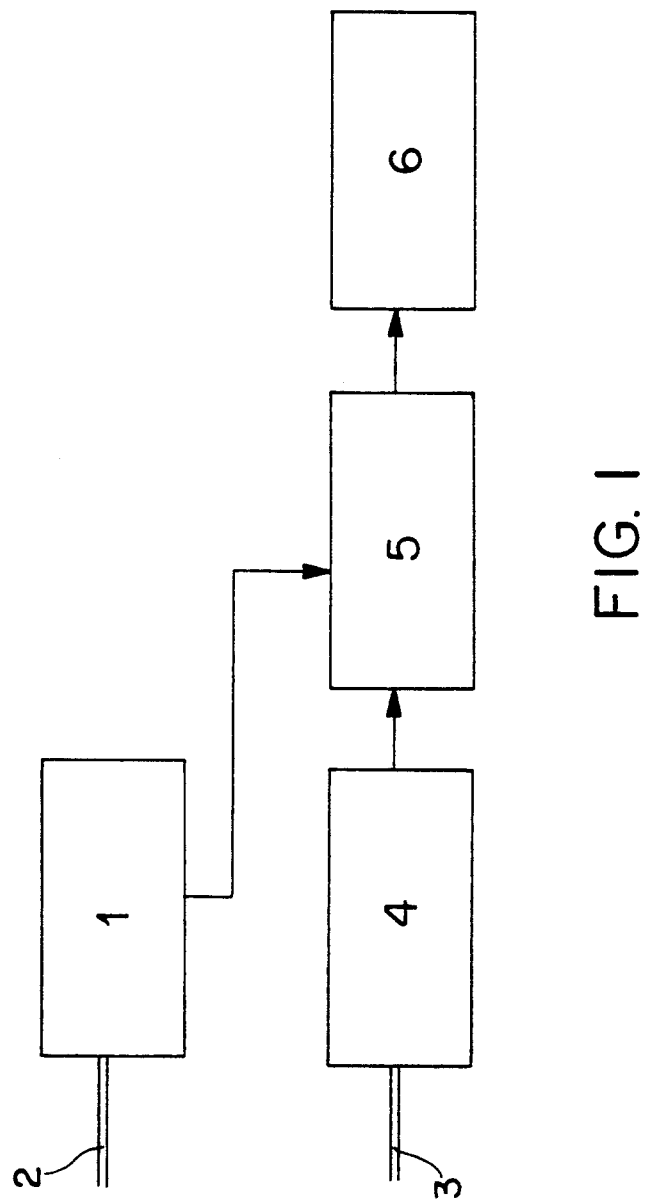
FIG. 1 is a block diagram representing the fundamental parts of the apparatus object of the present invention.

Accordingly, a first object of this patent application concerns a multiple wavelength pulsed light spectrophotometer for non-invasive monitoring, as illustrated by FIG. 1 herein, which comprises the following parts:

1. a light source emitting radiation in the near I. R., consisting of a lamp powered by A.C.-timed pulses;

2. a means of conducting the light to an organ to be monitored;

3. a means of conducting the light from the monitored organ;

4. a detector of at least four radiations with significant wavelengths for the parameters to be measured, from all those which have been supplied from the source and propagated through the organ;

5. an amplifier for converting the radiation pulse signal to a readily analyzed continuous signal and correcting for variations due to fluctuations of the source; and 6. an acquisition system including a microprocessor adapted to permity instantaneous computation of the values of the detected physiological parameters taking into account the light diffusion effects.

A particular embodiment of this invention will be now described by way of non-limitative example.

DESCRIPTION OF THE PREFERRED EMBODIMENT

Light Source

Figure 2:
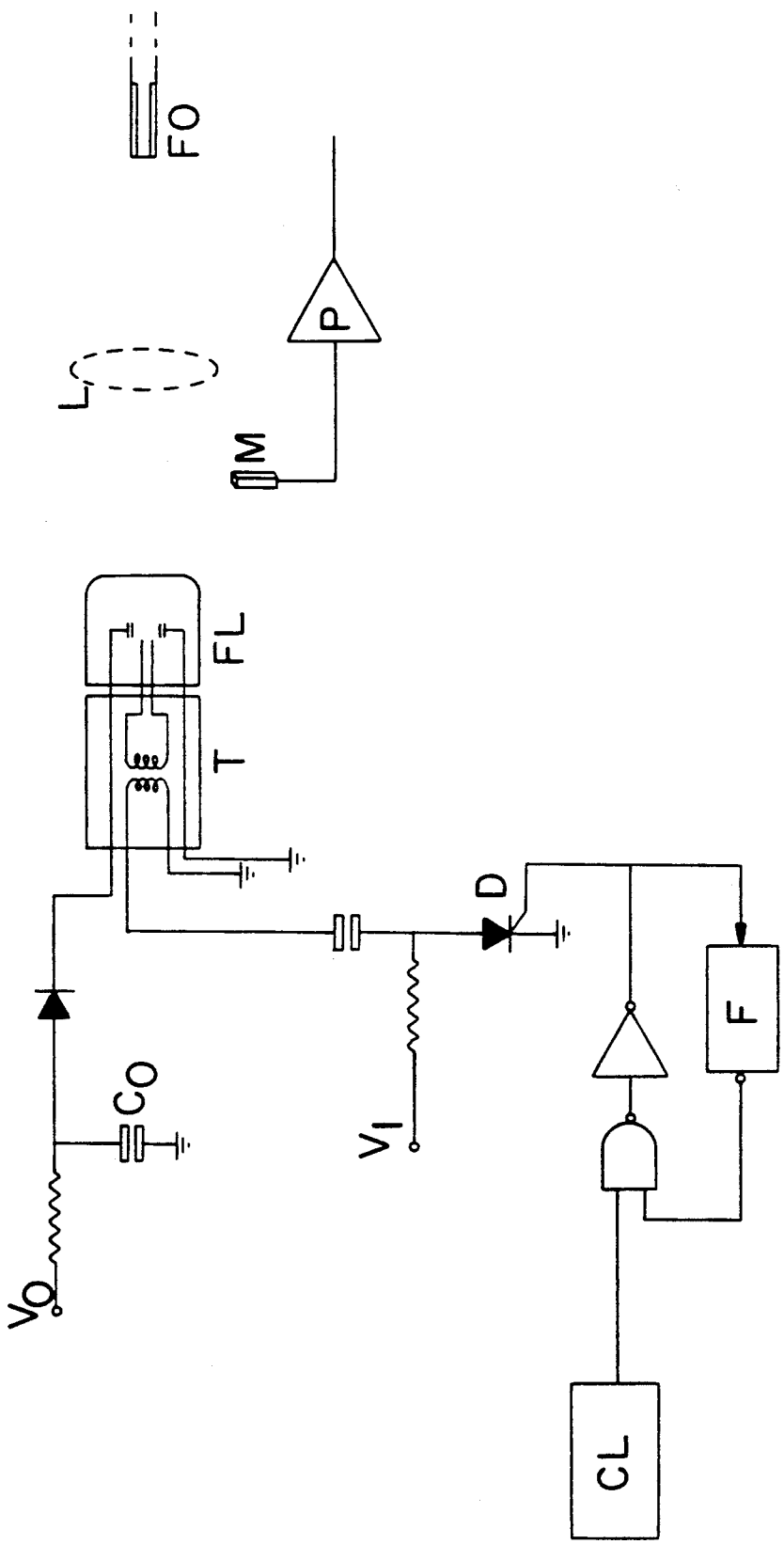
FIG. 2 is a detailed circuit diagram of the powering of the flash light source.

A circuit diagram is shown in FIG. 2 of the circuitry for energizing a xenon flash lamp (Type EGeGFx200 or the like).

Power for the light flash is supplied by a capacitor $C_o$ charged to a voltage level $V_o$. The capacitor is discharged through the lamp on receiving a trigger pulse.

The triggering pulse is provided by a controlled diode D via a transformer T (Model FY604 by EGeG) driven by a clock CL in synchronization with the mains. Each time that a pulse reaches the lamp, the shaper F will block the successive clock pulses for a set time period which may be varied at will.

During the tests carried out thus far, this time period was 125 ms and/or 250 ms.

The reference character M denotes a photodiode for monitoring the light from the lamp, and P denotes the output preamplifier. The light from the lamp is directed to a fiber optic FO by a glass lens system L.

A viable variation of the foregoing scheme utilizes instead a high brilliance lamp which is DC powered through a conventional power supply (the lamp being a 75-200 W xenon lamp of the Osram XBO Type); a chopper is placed in front of the fiber optic which is rotated synchronously with the mains.

Of course, this choice of a light source involves a modified implementation of the electronic amplifying circuitry, the duration of the light pulses being here longer than that of a light flash.

Light Conducting Means

The light is conducted to the organ to be monitored by a flexible optical fiber of transparent glass and/or plastic material having a diameter in the 2 to 10 mm range. The light emerging from the tissues is picked up by another optical fiber generally of the same size. The optical fibers are brought to rest on the tissue of the organ to be monitored such as to ensure a good contact, generally at a distance of a few centimeters from each other.

To this aim, for monitoring an organ of an individual, the device disclosed in U.S. Pat. Nos. 4,321,930 and 4,380,240 may be used to advantage.

Due to the high diffusion effect prevailing, it is immaterial whether the two fibers are aligned or form an angle therebetween which may be of as much as 180°.

Detector

Figure 3:
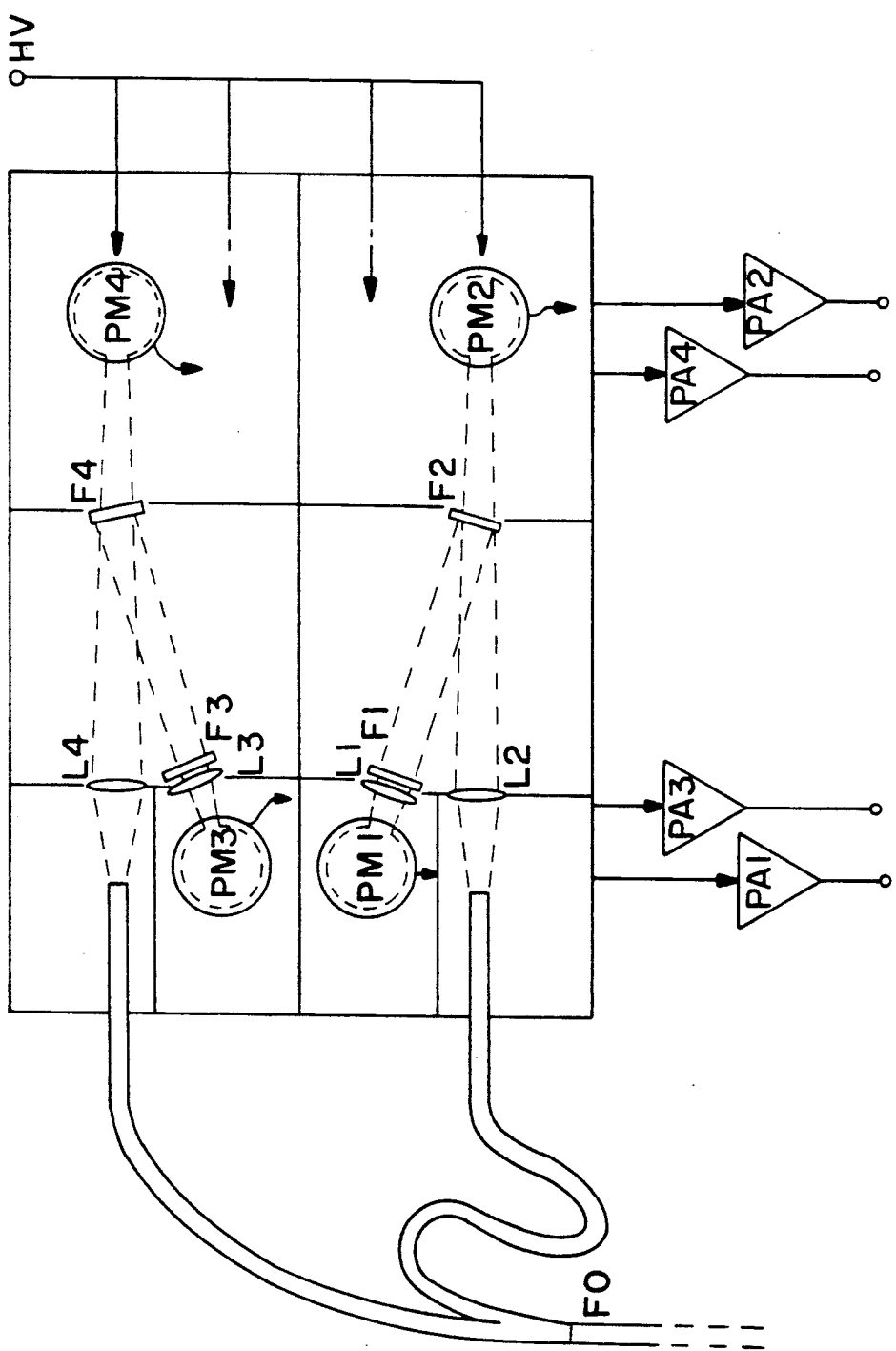
FIG. 3 is showing the positions of the light detectors.

FIG. 3 illustrates the detector arrangement. The incoming light from the region being monitored and flowing through the optical fiber FO first branches out in two, and then illuminates the photocathodes of four photomultipliers PM1, PM2, PM3, PM4 after going through interference filters F1, F2, F3, F4 the front faces whereof also form an excellent mirror.

Lenses L1, L2, L3, L4 focus the light onto the photocathode. The light path is indicated in dash lines. The photomultipliers (R928 or R936 by Hammatsu), which are particularly responsive in the region of the near I.R., are supplied with a voltage HV which may be varied or programmed in the 500 to 1,100 V range through separate dividers.

From the photomultiplier anodes a signal is picked up on resistors of relative low value ($<3K\Omega$) to maintain a good passband ($>1$ MHz), and the signal is amplified by preamplifiers PA1, PA2, PA3, PA4 powered by rechargeable batteries or by a separate power supply having a high immunity to noise, in order to avoid electromagnetic inductions from voltage discharges and coming over the mains. The batteries are recharged automatically. A different, simpler mount for the optics is to be obtained by using a four-legged fiber optic to illuminate the four photomultipliers separately. The interference filters employed have a mid-amplitude bandwidth ranging from 4 to 25 nm (preferably of 10 nm) centered in between 700 and 950 nm and preferably on 750, 800, 850 and 900 nm, respectively, (alternatively, on 750, 820, 850 and 900 nm, for example).

It would be possible to increase the number of the channels up to five or six, or even above, to thereby enhance the quantitative assessment of the scattering effects.

Amplifier

Figure 4:
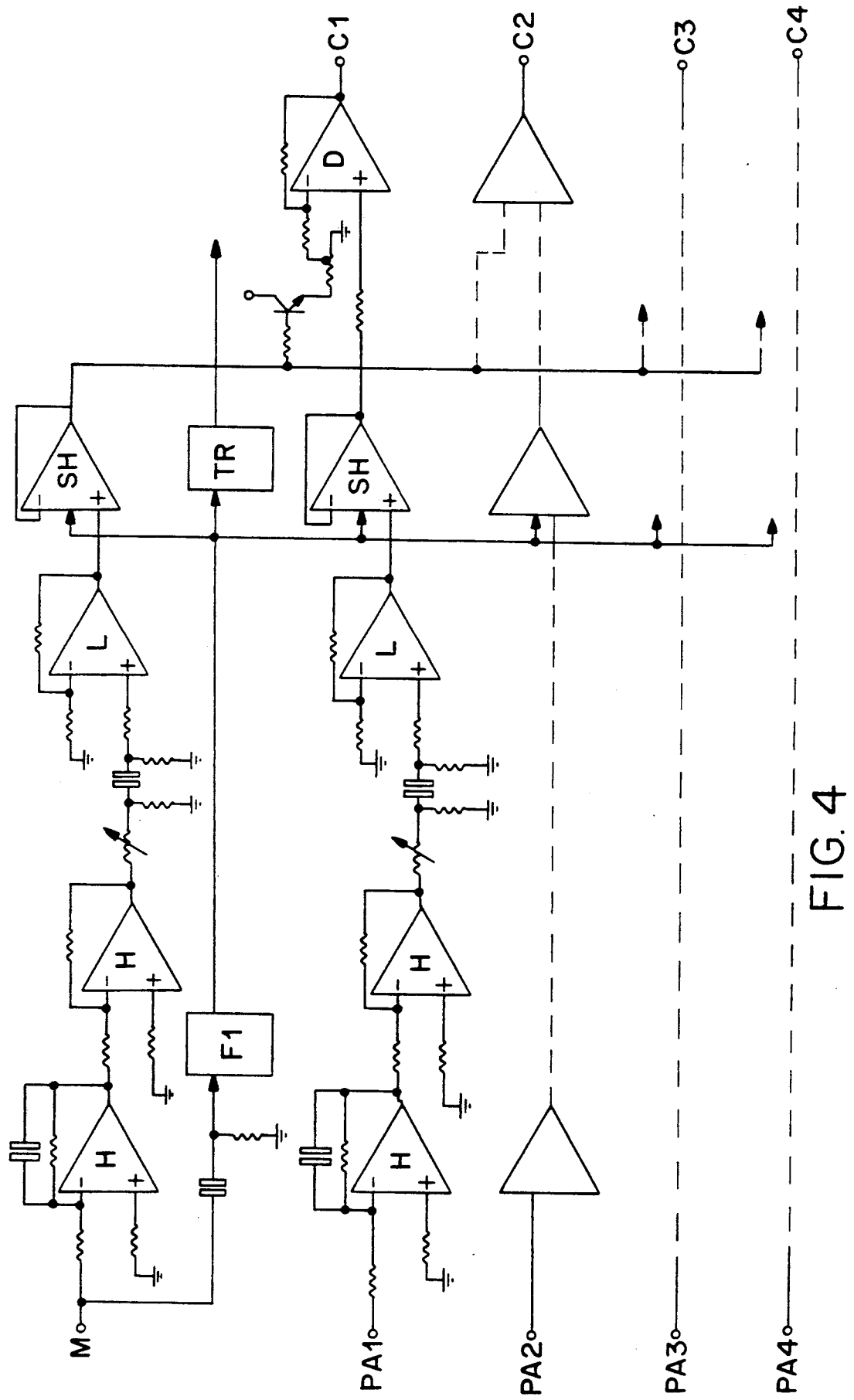
FIG. 4 is a detailed circuit diagram of the amplifiers system and of the sampling system of the signals for the computer.

Shown in FIG. 4 is an embodiment of the amplifier system and sampling circuitry for acquisition to the computer.

The signals from each of the channels, i.e. that from the photodiode M of the light source and those from the preamplifiers PA1, PA2, PA3, PA4, are amplified by a system of fast amplifiers formed of two inverters H, the first of which also functions as a shaper to determine a fixed upgoing time ($\pm 2$ $\mu$s) by means of the integrating capacitor provided on the feedback.

The two inverters are followed by a slower stage L and a sample-and-hold sampler SH. The control signal to the sampling circuit is supplied by a shaper F1 which, in turn, generates a trigger signal TR to control the computer acquisition sequence.

The individual channels are compared with the monitor in the differential stage D, so as to eliminate signal fluctuations due to the source oscillations. The signals C1, C2, C3, C4 thus obtained and the trigger signal TR are supplied to the acquisition system.

Acquisition System

Figure 5:
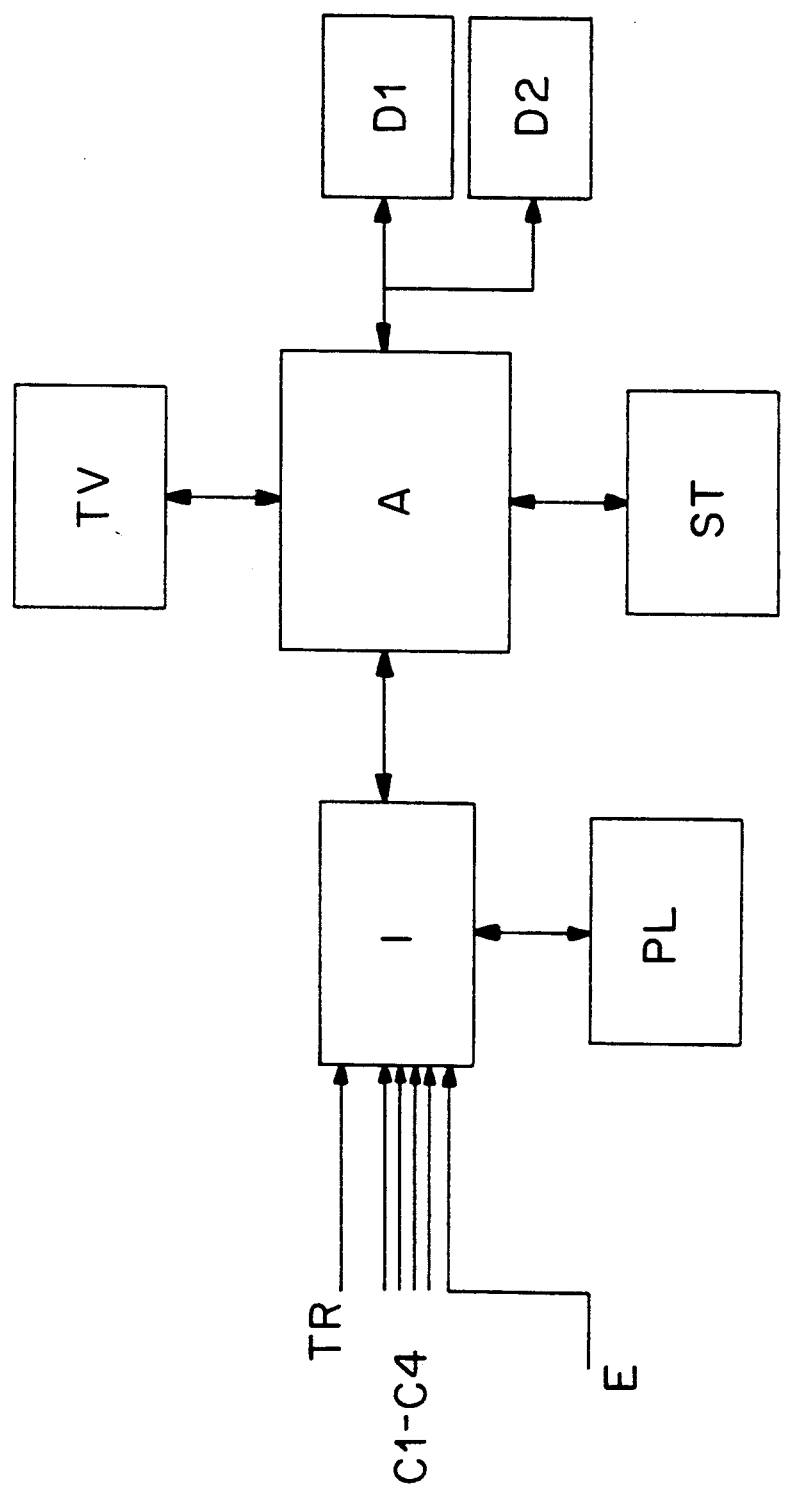
FIG. 5 is a block diagram of the computer system used to collect the signals and of its interface with the light detectors through an analogic/digital converter.

Shown diagramatically in FIG. 5 is a viable embodiment of the acquisition system for the instrument. A microprocessor A, 6502 from Apple II is employed with a commercial ISAAC I/O System I from Cyborg Co. capable of converting many analog signals sequentially and then passing them to the microprocessor.

The ISAAC system also allows analog signals to be passed to an external plotter PL to provide plots of the data obtained.

The microprocessor is connected to two disk drivers D1 and D2, a printer ST, and to the display TV. The storage capacity of the microprocessor employed is of 48 kilobytes. Also used is an additional 128 kibytres high-speed storage card which operates as a virtual disk. The same functions may be performed, of course, practically by any other microprocessor having comparable operating capabilities. The signal TR from the monitor (indicated at M in FIGS. 2 and 4) initiates the acquisition sequence. Once the data are transferred to the computer memories, it becomes possible to display, either on line or some time afterwards, the plots by calculating the values of the recorded physiological parameters, such as the hematic volume, hemoglobin oxygen saturation, and redox level of cytochrome-c-oxidase, through an algorithm which utilizes the instantaneous value of the signal at the four wavelengths.

The parameters of this calculation are obtained by an optimization process of the values calculated according to the theoretical model (D. V. Luebbers, Advances in Exp. Medicine and Biology, 37A, 45-54, 1973) and the experimental data.

In addition to the signals from the channels C1-C4, several other magnitudes from other instruments (E) are acquired.

Practically, the presence of scattering, the apparent optical density (OD app) at a given wavelength ($\lambda$) is represented by a monotonic function of absorbance (A) due to the presence of chromophores in the boiological tissue. This function can be approximated by the polynomial expression:

$$OD_{app} = C_{1\lambda} + C_{2\lambda}A - C_{3\lambda}A^2$$

where $C_{1\lambda}$, $C_{2\lambda}$, $C_{3\lambda}$, are dependent from scattering. The value of A is calculated by the addition of absorbances due to hemoglobin and cytochrome aa3 as measured in vitro. As a function of the parameters of interest, the heme value V, the hemoglobin oxygen saturation O, and the redox state of cyt aa3, R, it can be expressed:

$$A(\lambda) = a_{1\lambda}V + a_{2\lambda}O + a_{3\lambda}R + a_{0\lambda}$$

where $a_{0\lambda}$, $a_{1\lambda}$, $a_{2\lambda}$, $a_{3\lambda}$, are know with great precision from spectroscopic measurements in vitro, and $$V = [Hb] + [Hb\,O_2]$$

and $$O = [Hb\,O_2] - [Hb].$$

Scattering amplitude is also a function of blood volume S, so that the coefficients $C_{1\lambda}$, $C_{2\lambda}$ and $C_{3\lambda}$ can be expressed a function of S. By a comparison of calculated curves with experimental data it results:

$$C_1 \simeq 0;\ C_{2\lambda} = C_{20\lambda} \times (1 + \gamma S);\ C_{3\lambda} = C_{30\lambda}(1 + \gamma S)$$

The values of $C_{20\lambda}$, $C_{30\lambda}$, $\gamma$ are obtained by this comparison. The physiological parameters O,V,R are determined with a precision depending from errors affecting the values of the constants calculated by this procedure. Practically, the evaluation of O results to be sufficiently precise, while V and R are affected by a large error due to the necessity of subtracting large contributions of scattering effects, and because these effects widely fluctuate from subject to subject.

The precision is much better when the variations of optical density are considered with respect to an initial value obtained on the same subject.

In this case $$\delta OD_{app}(\lambda) = \delta(C_{2\lambda}A - C_{3\lambda}A^2)$$

and

-continued $$\delta OD(\lambda) = (C_{2\lambda} - 2C_{3\lambda}A)(a_{1\lambda}\delta V + a_{2\lambda}\delta O + a_{3\lambda}\delta R) + app$$

$$A\gamma(C_{20\lambda} - AC_{30\lambda})\delta S$$

Since in practice $\gamma$ is small and $\delta S$ is of the same order of magnitude of $\delta V$, in this case the corrections due to the scattering variations are small, and the values of O, V, and R can be evaluated with a relatively small error.

It will be appreciated that various data processing programs may be utilized with the microprocessor which allow some of the noise to be filtered out, spikes caused by instantaneous shifts in the plots due to changes in the fiber optics-to-tissue contact to be detected and corrected, and so forth.

The instrument just described affords the following advantages:

1. pulse operation makes the ambient light background virtually negligible;
2. the monitor enables correction for any fluctuations in the source intensity;
3. the light measurement transmitted on at least four wavelengths enables computation of the hemoglobin content of the tissues being observed, of its oxygenation level, and of the oxyreduction state of cytochrome-c-oxidase;
4. real time processing becomes feasible through a calculation process which enables correction at any time instant of the absorption values for the effect due to light diffusion;
5. the measurement stability is enhanced by the use of a separate power supply for the preamplifiers and by synchronization of the source with the mains;
6. the microprocessor permits the detection and correction of any instantaneous shifts in the plots due to variations in the contact between the fiber optics and tissue; and
7. it becomes possible to correlate the measurements taken by absorption in the near I.R. with those derived from other instruments.

Figure 6:
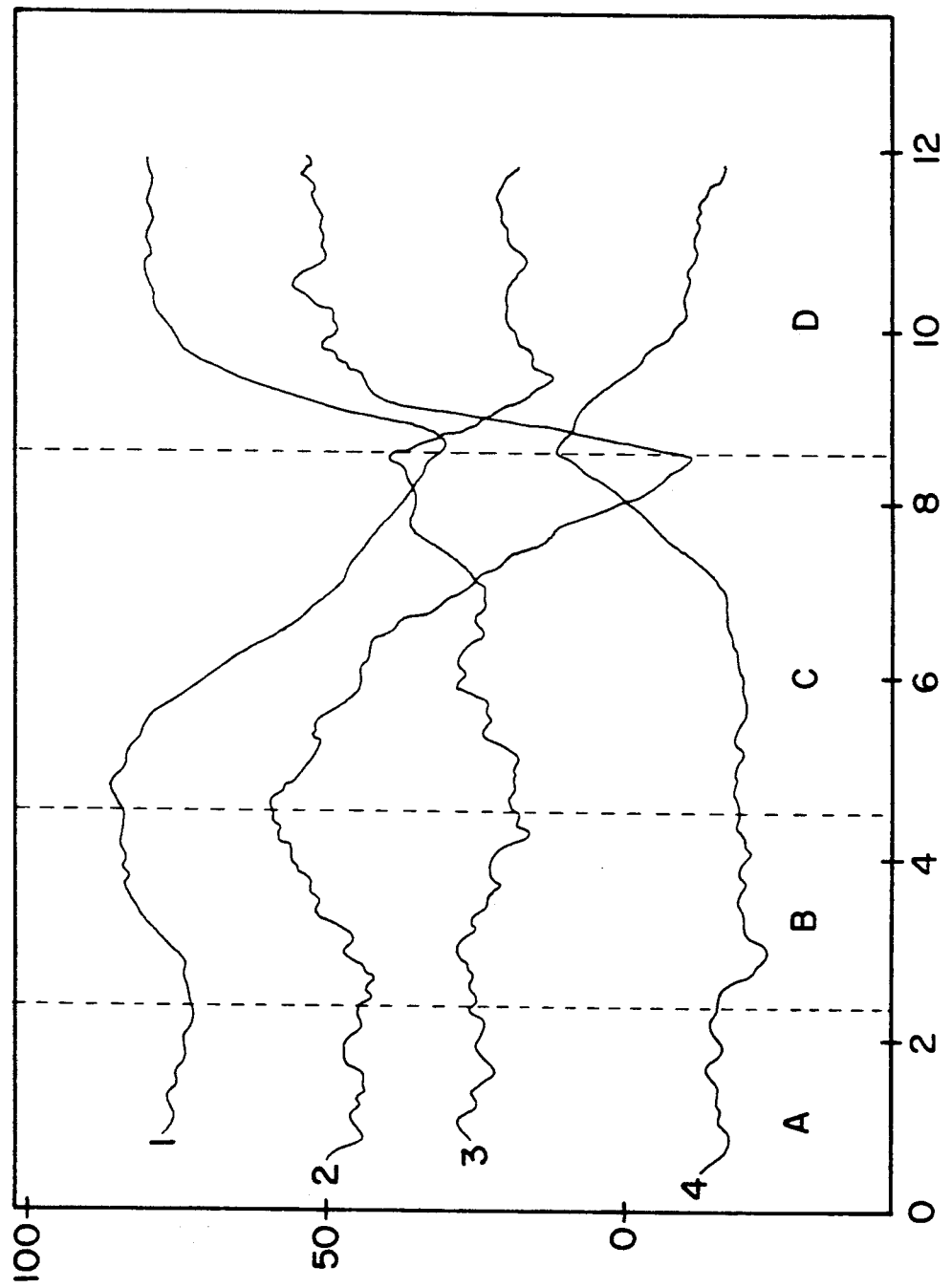
FIG. 6 and 7 are showing some typical curves of oxygen saturation of hemoglobin, oxydation of the cytochrome-c-oxydase and of blood volume measured by means of the invention's apparatus in the encephalic region at different respiratory activities in comparison with oxygen level measured by a skin electrode.
Figure 7:
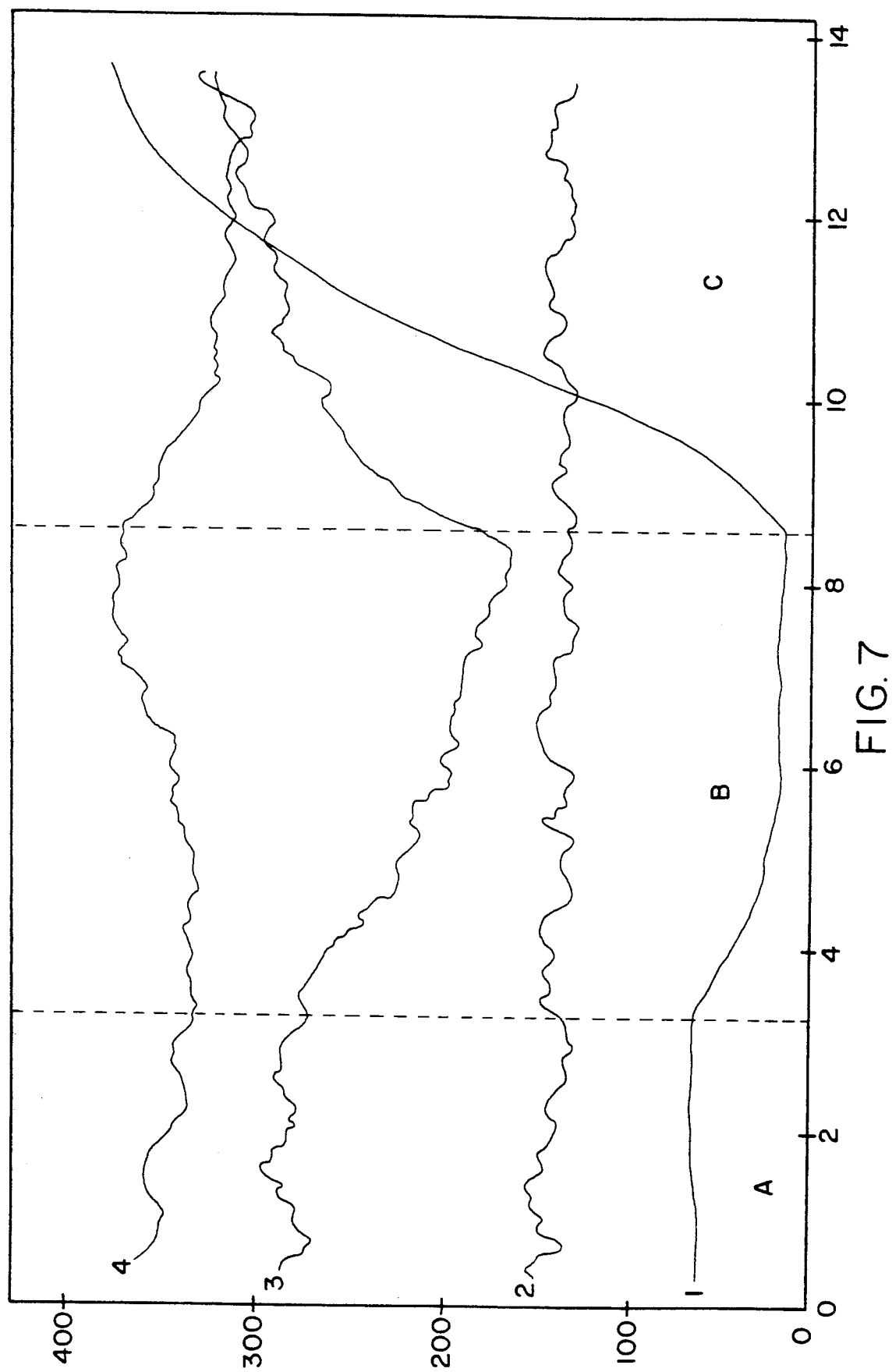

By way of example FIGS. 6 and 7 are showing the recorded plots for the aforesaid parameters as measured in the encephalon together with a measurement of the oxygen pressure at skin level taken with a transcutaneous electrode (radiometer, Model TCM 2).

FIG. 6 shows a typical plot obtained during changes in the respiratory activity (hyperventilation-apnea). On the abscissa is the time in minutes.

On the ordinate, an mmHg scale relating to curve 1 is reproduced on the left.

Section A of the Figure corresponds to a condition of normal breathing, section B to a condition of hyperventilation, section C to a condition of apnea, and section D again to a condition of normal breathing.

The curve 2 is a measure of the hemoglobin saturation level, the curve 3 is a measure of the cytochrome-c-oxidase oxydation state, and the curve 4 is a measure of the hematic volume.

The oxygen level in the arterial blood of the arm has been recorded for reference by means of a transcutaneous electrode (Curve 1).

During the apnea, the hemoglobin saturation level at arterial level drops from 95% down to about 55%, the oxireductive state of cytochrome-c-oxidase drops by about 15% from an estimated level of about 80%, and the hematic volume increases to 12% from 10%.

It should be noted that the value of this parameter depends to some extent on the model assumed and the assumed values for the cerebral hematocrit, generally lower than the peripheral one (M.E. Phelps et al., J. Appl. Physical 35, 275-280, 1983).

FIG. 7 shows instead a typical plot obtained during inhalation of different gas mixtures (air, pure oxygen, hypoxic mixture).

On the abscissa is the time in minutes.

On the ordinate, there is reproduced an mmHg scale relating to the curve 1.

In section A of the Figure, the condition is that of air breathing, in section B of breathing a hypoxic mixture ($O_2$ 10%, $N_2$ 90%), and in section C the condition is that of breathing pure $O_2$.

The curve 2 is a measure of the oxidative state of cytochrome-c-oxidase, the curve 3 is a measure of the hemoglobin saturation level, and the curve 4 is a measure of the hematic volume.

Here too, the level of $O_2$ in the arterial blood of the arm has been recorded for reference by means of a transcutaneous electrode (Curve 1).

While breathing the hypoxic mixture, the oxidative state of cytochrome-c-oxidase does not vary appreciably, the saturation level of hemoglobin decreases from 90% to about 65%, and the hematic volume changes from 10% to about 11%.

Based on the general scheme outlined above, a more complex instrumentation may be provided to simultaneously monitor different regions of one and the same organ.

Figure 8:
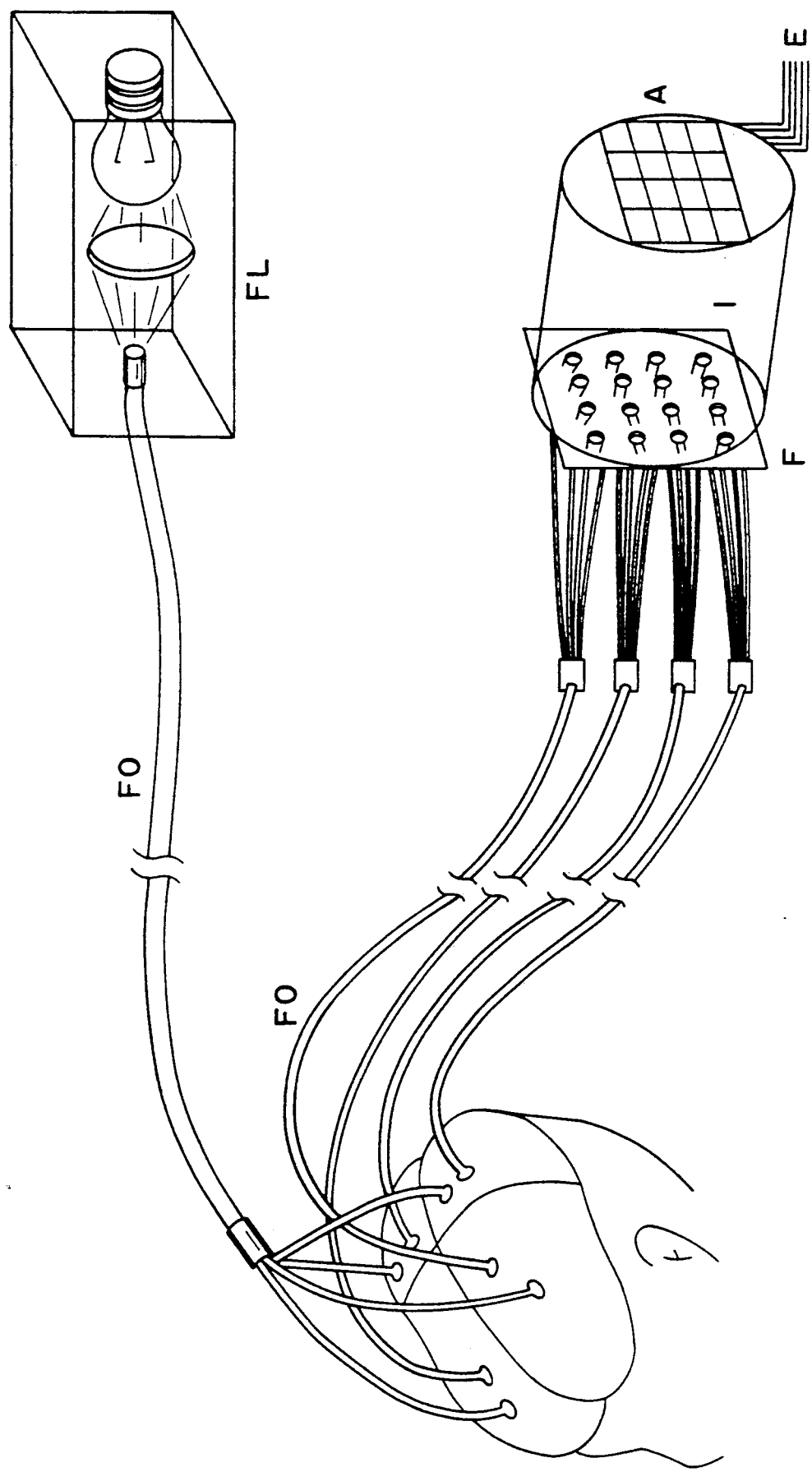
FIG. 8 is a pictorial view of the optical fibers disposition for a simultaneous monitoring of different regions of a same body section.

The arrangement of the optical fiber FO for such an instrument is shown in FIG. 8 by way of example. Shown schematically at FL is the source of light, which may be embodied as in the preceding example.

Multiple leg fibers are used, and in each region the transmitted light is measured at at least four wavelengths.

The several detectors may be replaced advantageously with a picture intensifier I (e.g. Thomson-CSF 9403) coupled with a cluster of solid state silicon detectors A.

The filter system F may be replaced with a single filter varying in the 750 to 900 nm.

The electric signals from the detectors E should then be processed by a system of amplifiers similar to the one discussed hereinabove.

A more complex instrument like the one disclosed herein would enable mapping of the metabolism and vascular state of cerebral cortex in keeping with the most up-to-date imaging methodics.

Also provided by this invention is a spectrophotometric method for measuring circulatory and local metabolism parameters in living organs by non-invasive monitoring, which utilizes the spectrophotometer described in the foregoing.

We claim:

1. An improved multiple wavelength light spectrophotometer for non-invasive monitoring of a body organ in vivo comprising:
    (a) a single light source emitting radiation at at least four near infrared wavelengths including a lamp powered by AC-timed pulses;
    (b) an optical fiber transmitting the near infrared radiation emitted from said single light source to a body organ;
    (c) an optical fiber receiving near infrared radiation transmitted through the organ by said transmitting optical fiber (b) and conducting the received infrared radiation to a radiation detector (d), which receiving optical fiber is disposed in relation to said transmitting optical fiber (b) so that the two optical fibers are aligned or form an angle therebetween of up to 180°;
    (d) a radiation detector having means for branching the radiation conducted from optical fiber (c) into at least four different wavelengths, comprising a system of at least four interference filters and complimentary photomultipliers whereby at least four individual signals corresponding to said at least four different wavelengths are produced and transmitted to amplifier means (e);
    (e) amplifier means for converting said at least four individual signals to continuous signals; and
    (f) data acquisition means connected to said amplifier means for converting the continuous signals into display signals representing values of physiological parameters, including a microprocessor utilizing the following algorithm to correct the display signals for light diffusion effects:

$$\delta OD_{app}(\lambda) = (C_2\lambda - 2C_3\lambda A)(a_1\lambda \delta V + a_2\lambda \cdot \delta O + a_3\lambda \delta R) + A\gamma(C_{2o}\lambda - AC_{3o}\lambda)\delta S.$$

wherein
$OD_{app}$ is the apparent optical density at a given wavelength ($\lambda$);
A is absorbance;
S is the blood volume;
R is the redox state of cyt $aa_3$;
O is the hemoglobin oxygen saturation; and
V is the heme value.

2. An improved multiple wavelength light spectrophotometer as claimed in claim 1 wherein the light source is a xenon flash lamp.

3. An improved multiple wavelength light spectrophotometer as claimed in claim 1 wherein the interference filters have a mid-height bandwidth within the range of 4 to 25 nm centered in the 700 to 950 nm range.

4. An improved multiple wavelength light spectrophotometer as claimed in claim 3 wherein the interference filters have a mid-height within the range of 4 to 25 nm centered at 750, 800, 850 and 900 nm, respectively.

5. An improved multiple wavelength light spectrophotometer as claimed in claim 3 wherein the interference filters have a mid-height bandwidth within the range of 4 to 25 nm centered at 750, 820, 850 and 900 nm, respectively.

6. An improved multiple wavelength light spectrophotometer for non-invasive monitoring of a body organ in vivo comprising:
    (a) a single light source emitting radiation at at least four near infrared wavelengths including a lamp powered by AC-timed pulses;
    (b) an optical fiber transmitting the near infrared radiation emitted from said single light source to a body organ;
    (c) an optical fiber receiving near infrared radiation transmitted through the organ by said transmitting optical fiber (b) and conducting the received infrared radiation to a radiation detector (d), which receiving optical fiber is disposed in relation to said transmitting optical fiber (b) so that the two optical fibers are aligned or form an angle therebetween of up to 180°;

(d) a radiation detector having means for branching the radiation conducted from optical fiber (c) into at least four different wavelengths, comprising a system of a single interference filter variable in the range of 750 to 900 nm and complimentary photomultiplier whereby at least four individual signals corresponding to said at least four different wavelengths are produced and transmitted to amplifier means (e);

(e) amplifier means for converting said at least four individual signals to continuous signals; and (f) data acquisition means connected to said amplifier means for converting the continuous signals into display signals representing values of physiological parameters, including a microprocessor utilizing the following algorithm to correct the display signals for light diffusion effects:

$$\delta OD_{app}(\lambda) = (C_2\lambda - 2C_3\lambda A)(a_1\lambda\delta V + a_2\lambda\delta O + a_3\lambda\delta R) + A\gamma(C_{2o}\lambda - AC_{3o}\lambda)\delta S.$$

wherein $OD_{app}$ is the apparent optical density at a given wavelength ($\lambda$);

A is absorbance;

S is the blood volume;

R is the redox state of cyt $aa_3$;

O is the hemoglobin oxygen saturation; and

V is the heme value.

* * * * *